United States Patent [19]
Huang et al.

[11] Patent Number: 5,332,705
[45] Date of Patent: Jul. 26, 1994

[54] REGENERATION OF ACETYLENE CONVERTER CATALYSTS BY HYDROGEN STRIPPING

[75] Inventors: Yao-Jyh Huang, Houston, Tex.; Chong F. Shun, Bridgewater, N.J.; Lawrence G. Daniel, Crosby; Edgar L. Mohundro, Baytown, both of Tex.; John E. Hartgerink, Baton Rouge, La.

[73] Assignee: Exxon Chemical Patents Inc., Linden, N.J.

[21] Appl. No.: 901,321

[22] Filed: Jun. 19, 1992

[51] Int. Cl.$^5$ .............. B01J 23/96; B01J 38/10; C07C 5/08; C07C 7/167
[52] U.S. Cl. .................. 502/53; 585/259; 585/260; 585/273
[58] Field of Search .............. 502/53; 585/260, 259, 585/273

[56] References Cited

U.S. PATENT DOCUMENTS

| 2,946,829 | 7/1960 | Likins et al. | 585/260 |
| 3,812,057 | 5/1974 | Morgan et al. | 585/260 |
| 3,912,789 | 10/1975 | Frevel et al. | 585/260 |
| 4,227,025 | 10/1980 | Montgomery | 585/259 |
| 4,388,479 | 6/1983 | Gryaznov | 568/828 |

FOREIGN PATENT DOCUMENTS

| 907348 | 10/1962 | United Kingdom | 502/53 |
| 1158418 | 7/1969 | United Kingdom | 502/53 |

Primary Examiner—Paul E. Konopka
Attorney, Agent, or Firm—Linda K. Russell

[57] ABSTRACT

An improved method for regenerating acetylene hydrogenation catalysts which does not require an oxygenation step is provided. The method may be used to regenerate any acetylene hydrogenation catalyst; however, the method is particularly advantageous when used with a palladium based catalyst which has been used to remove acetylenic contaminants from ethylene.

6 Claims, 4 Drawing Sheets

REGENERATION OF ACETYLENE CONVERTER CATALYSTS BY HYDROGEN STRIPPING

BACKGROUND OF THE INVENTION

Field of the Invention

The present invention relates to an improved method for regenerating catalysts that have been used to remove acetylenic contaminants from olefin product streams. More particularly, the present invention relates to an improved method for regenerating palladium-containing catalysts that have been used to remove acetylenic contaminants from ethylene.

Product streams of liquid or liquefiable olefins and diolefins typically are contaminated with small amounts of acetylenic impurities. For example, the ethylene/ethane fraction in an ethylene plant typically contains 0.5–2.0% acetylenic impurities. Such acetylenic contamination is undesirable because acetylene tends to poison the catalysts that are used to convert ethylene to polyethylene. Acetylene also can form metal acetylides which are explosive and which may contaminate the equipment that is used to process such product streams.

It is known that acetylenic impurities can be selectively hydrogenated and thereby removed from such a product streams by passing the product stream over a catalyst (an "acetylene hydrogenation catalyst") in the presence of hydrogen; however, the hydrogenation process typically results in the deposition of a green oil on the catalyst which deactivates the catalyst. Therefore, acetylene hydrogenation processes typically include an oxygenation step or a "burn" step to remove the deactivating carbonaceous residues from the catalyst followed by a hydrogen reduction step to reactivate the catalyst. See, e.g., U.S. Pat. No. 3,812,057 to Morgan and U.S. Pat. No. 4,425,255 to Toyoda.

An oxygenation step followed by hydrogen reduction normally is effective to regenerate an acetylene hydrogenation catalyst; however, there are many disadvantages to the use of an oxygenation step during regeneration of such catalysts.

First, when oxygen and hydrogen come together under the conditions used to regenerate the catalyst, an exothermic reaction is produced which may result in uncontrolled temperature runaway. Thus, before the regeneration is performed, it is necessary to purge the catalyst of hydrogen and hydrocarbons using an inert gas, such as nitrogen gas, both before and after the oxygen-containing stream is introduced. The purging process is both tedious and time consuming. Furthermore, if the regeneration is performed in situ, the concentration of oxygen in the regeneration gas stream must be regulated carefully in order to avoid reactor temperature run-away. It would be advantageous if acetylene hydrogenation catalysts could be regenerated using a method which did not require such time consuming purging and monitoring.

The use of an oxygenation step during regeneration of an acetylene hydrogenation catalyst also presents an environmental concern due to the resulting emission of carbon monoxide, carbon dioxide, and unburned hydrocarbons. The hydrocarbon residue that remains on the catalyst can comprise up to 10 wt % of the catalyst. The oxygenation of this amount of residue results in the emission of a substantial amount of carbon monoxide and carbon dioxide. In addition, the emission during oxygenation may contain approximately 6–10% of unburned hydrocarbons. It would be advantageous if acetylene reduction catalysts could be regenerated in a manner that did not result in such environmentally undesirable emissions.

Regeneration of acetylene hydrogenation catalysts using an oxygenation step also is undesirable because the oxygenation step has a negative impact on the life of the catalyst. A catalyst that has been used to hydrogenate acetylene typically must be regenerated once every one to three months. Acetylene hydrogenation catalysts are heat sensitive, and exposure to excessive heat decreases the activity of the catalyst. The oxygenation step that is used in most regeneration processes typically is run at temperatures between about 371°–455° C. (700°–850° F.). The exposure of an acetylene hydrogenation catalyst to such high temperatures at such regular intervals takes a great toll on the life of the catalyst. It would be advantageous if the regeneration of such catalysts could take place at lower temperatures which reduced the thermal stress induced during the regeneration.

Some of these disadvantages can be avoided if the catalyst is regenerated ex situ, or outside of the reactor. However, the unloading and reloading of the reactor with the catalyst is a time consuming process. And even if the regeneration process is performed ex situ, the catalyst still must be purged with an inert gas both before unloading and after reloading the reactor. Thus, regardless of where the regeneration process takes place, significant reactor down time is required if the catalyst is regenerated using a process that includes an oxidation step.

For all of these reasons, it would be advantageous if acetylene reducing catalysts could be regenerated without an oxygenation step. One existing patent acknowledges that partial regeneration can be accomplished using a hydrogenation step alone. See col. 4, lines 16–35 of U.S. Pat. No. 3,912,789. However, this patent teaches that full regeneration of an exhausted catalyst requires an oxygenation step. Therefore, a process has yet to be developed that can fully regenerate acetylene reduction catalysts without the need for an oxygenation step.

SUMMARY OF THE INVENTION

The present invention provides an improved regeneration process for acetylene hydrogenation catalysts which does not require an oxygenation step. The present inventors have discovered that acetylene reduction catalysts can be fully regenerated by hydrogen stripping, alone, at relatively low temperatures. The present inventors also have discovered that palladium-containing catalysts that have been used to purify ethylene unexpectedly have a better selectivity to ethylene after they are hydrogen stripped according to the present invention.

DETAILED DESCRIPTION OF THE INVENTION

Figure 1:
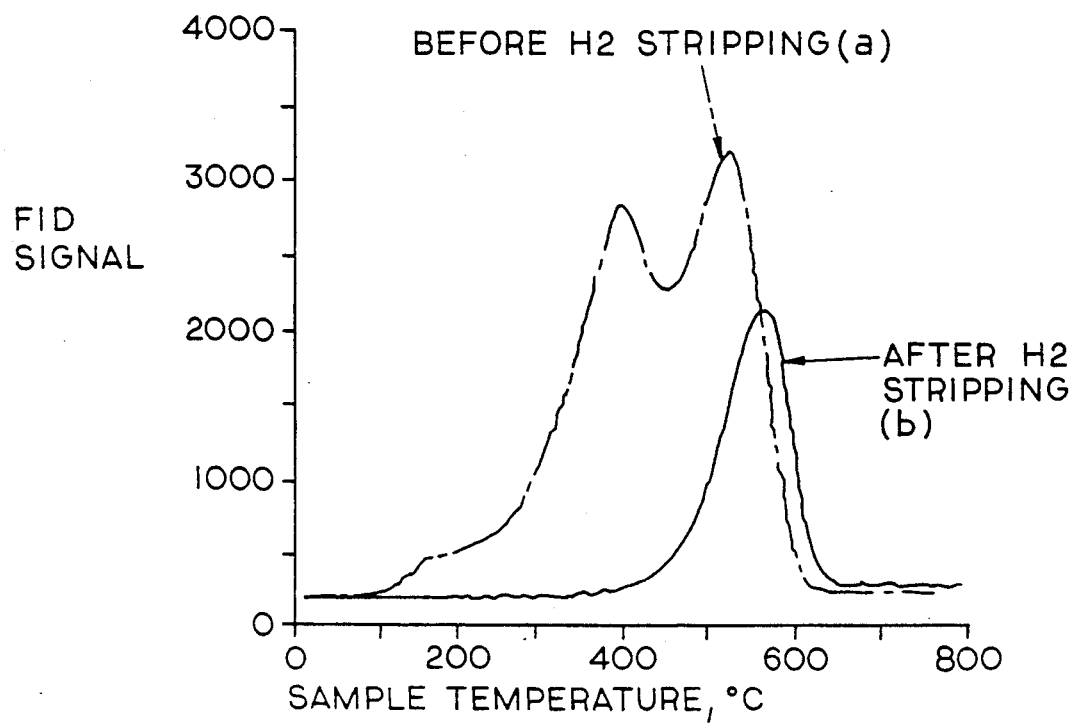
FIG. 1 is a chart showing the TPO spectra of the UCI G58B catalyst of Example 1 before (a) and after (b) hydrogen stripping.

According to the present invention, a spent acetylene hydrogenation catalyst is hydrogen stripped with a mixture of hydrogen and inert gas wherein the hydrogen concentration is between about 0.1-100%, preferably between about 5-10%. Since only 5-10% of the hydrogen in the stripping gas is required during the stripping process, any low value hydrogen source, preferably without carbon monoxide, can be employed. For example, hydrogen may be purchased and mixed fresh with an inert gas, or the hydrogen may come from another refining operation. For example, the overhead effluent from a demethanizer, which contains about 5% $H_2$ in $CH_4$ (normally used as fuel gas) may be one potential source for hydrogen. It also may be possible to recycle hydrogen that has already been used to regenerate the catalyst.

The percentage of hydrogen in the gas stripping mixture is not critical to the present invention. In the following examples, a mixture of inert gas and around 9-10% hydrogen was used. Any inert gas may be used in the mixture. The most commonly available and most inexpensive inert gas for use in the invention is nitrogen; therefore, nitrogen is a preferred inert gas for use in the present invention.

Although the following examples of the invention describe regeneration of palladium based acetylene reduction catalysts, one of skill in the art will recognize that the hydrogen stripping process of the present invention may be used to regenerate other types of catalysts that are used to hydrogenate acetylene. For example the present process could be used to regenerate acetylene hydrogenation catalysts which contain: Group VIII metals, such as nickel, cobalt, ruthenium, palladium, and platinum; Group VIB metals, such as chromium, molybdenum, and tungsten; or Group IB metals, such as copper, silver, or gold. However, the preferred catalyst for use in the present invention is a catalyst in which the primary active element is palladium, which comprises approximately 0.01-0.5% of the catalyst, preferably 0.02-0.05%. A palladium content higher than about 0.5% could deteriorate at the temperatures used in process of the present invention.

The stripping procedure should take place at a temperature ranging between about 260°-400° C. (500°-750° F.), preferably between about 315°-372° C. (600°-700° F.), and more preferably at about 350° C. (662° F.). In order to avoid deactivating a palladium based catalyst, or agglomerating the palladium, the temperature of the hydrogen stripping procedure should not exceed about 400° C. (750° F.).

The pressure at which the stripping takes place may not be critical; however, the stripping preferably should take place between about 0 Newtons/$m^3$ (0 psig and 2,068,428 Newtons/$m^3$ (300 psig), and more preferably between about 0 Newtons/$m^3$ (0 psig) and 344,738 Newtons/$m^3$ (50 psig). Lower cost sources having a low content of hydrogen typically are more readily available at lower pressures. In the following examples, pressures of about 2,068,428 Newtons/$m^3$ (300 psig) and 0 Newtons/$m^3$ (0 psig) were used. Similarly, the time period required for stripping is not critical. One of skill in the art will recognize that the amount of time needed for the stripping procedure can be determined by monitoring the amount of hydrocarbon present in the catalyst until a minimum plateau level has been achieved. In the following examples, the stripping time ranged between 16-24 hrs.

The flow rate of the hydrogen through the catalyst should be such that the linear velocity through the catalyst should be at least about 15.2 cm/second (0.5 feet/second). Lower velocities may be insufficient to achieve uniform regeneration of the catalyst.

The invention will be further elucidated by the following examples.

EXAMPLE 1

An aliquot of UCI G58B catalyst (Pd/$Al_2O_3$) after 200 hours of use was stripped with 10% $H_2$/Ar from room temperature to about 750° C. (1382° F.) at a heating rate of about 13° C./min (55° F.). The carbonaceous residues on the catalyst were analyzed both before and after hydrogen stripping by temperature programmed oxidation (TPO), which detected carbon oxide emission during the burn while the reactor temperature was linearly increased. The TPO spectra of the spent catalyst before and after hydrogen stripping were plotted as FIGS. 1(a) and (b), respectively.

Before hydrogen stripping, two types of carbonaceous residues were present on the catalyst. A peak at about 400° C. (750° F.) represents carbonaceous residues that were present on and/or near palladium. A peak at about 510° C. (950° F.) represents carbonaceous residues that were present on the supports. After hydrogen stripping, only one peak appeared at about 550° C. (1022° F.). The presence of only this single peak after hydrogen stripping indicated that the carbonaceous residues that were on and/or near the palladium were removed by the hydrogen stripping. Since acetylene conversion occurs mainly on palladium sites in the catalyst, the removal of carbonaceous residues from the palladium can re-expose the palladium active sites and recover the activity of the palladium. The hydrocarbons that are stripped off of the catalyst can be either recycled to the cracker or used as fuel gas.

Because hydrogen stripping does not remove all of the carbonaceous deposits from the supports, it is possible that an air burn may be required eventually in order to clean the supports to prevent restriction of flow rate, pressure, etc. However, the number of air burns that may be necessary to clean the supports in such a system will be much less than the frequent air burns that heretofore have been required to regenerate the catalyst. An infrequent air burn to clean the supports will be much less intrusive and damaging than the frequent, repetitive air burns required in current catalyst regeneration processes.

EXAMPLE 2

Figure 2:
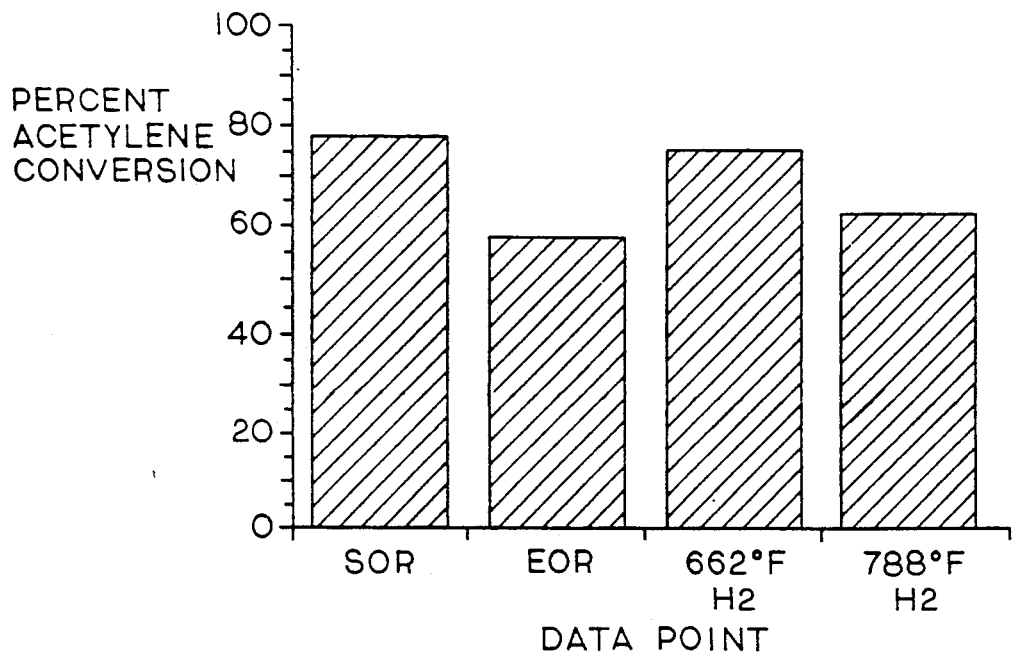
FIG. 2 is a bar graph comparing the catalyst activity of the BASF HO11 catalyst of Example 2 before and after hydrogen stripping. "SOR" under the first bar in the graph stands for activity at the start of the run. "EOR" under the second bar in the graph stands for activity at the end of the run. The bar above "662° F. H2" represents the activity of the catalyst after hydrogen stripping at about 350° C. (662° F.). The bar above "788° F. H2" represents the activity of the catalyst after further hydrogen stripping at about 420° C. (788° F.).
Figure 3A:
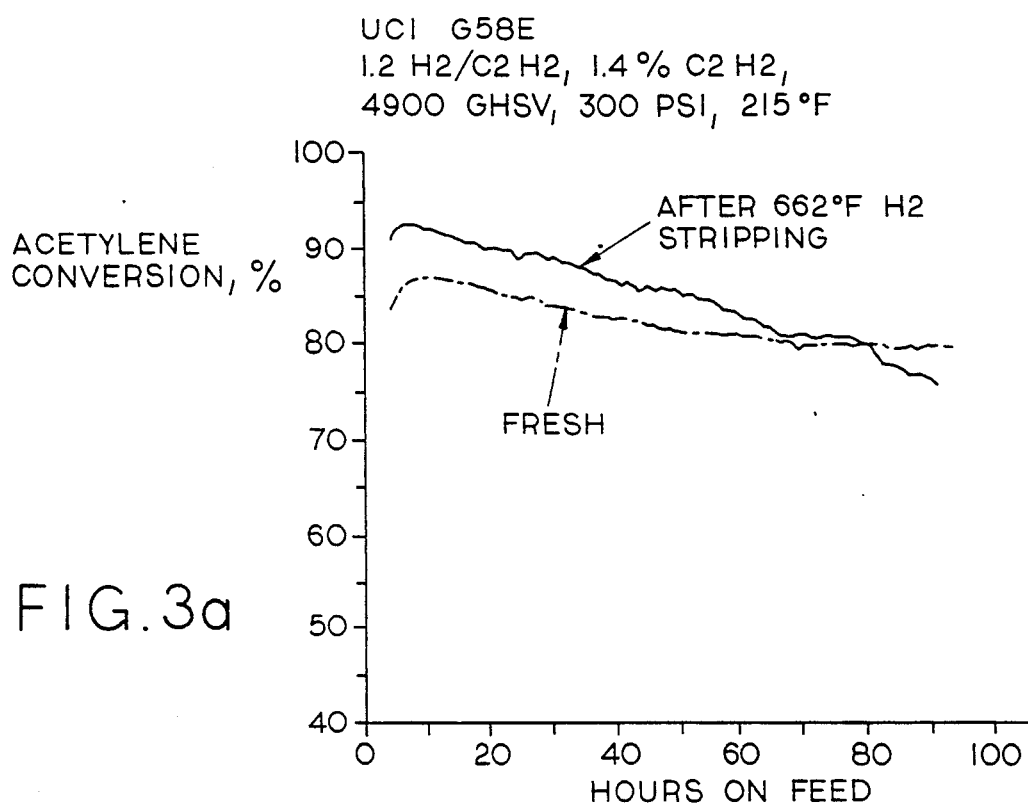
FIG. 3(a) is a graph comparing the acetylene conversion activity of the UCI G58E catalyst of Example 3 when fresh to the activity of that same catalyst after it has been hydrogen stripped according to the present invention at about 350° C. (662° F.).
Figure 3B:
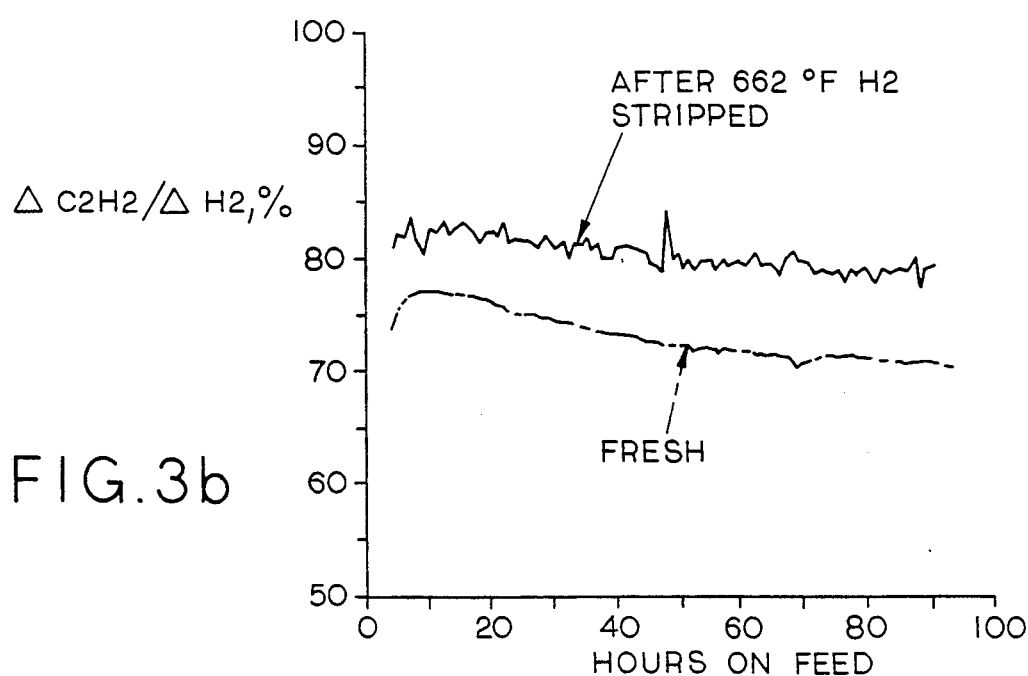
FIG. 3(b) is a graph comparing the deactivation rate of the fresh and stripped catalyst of Example 3.
Figure 3C:
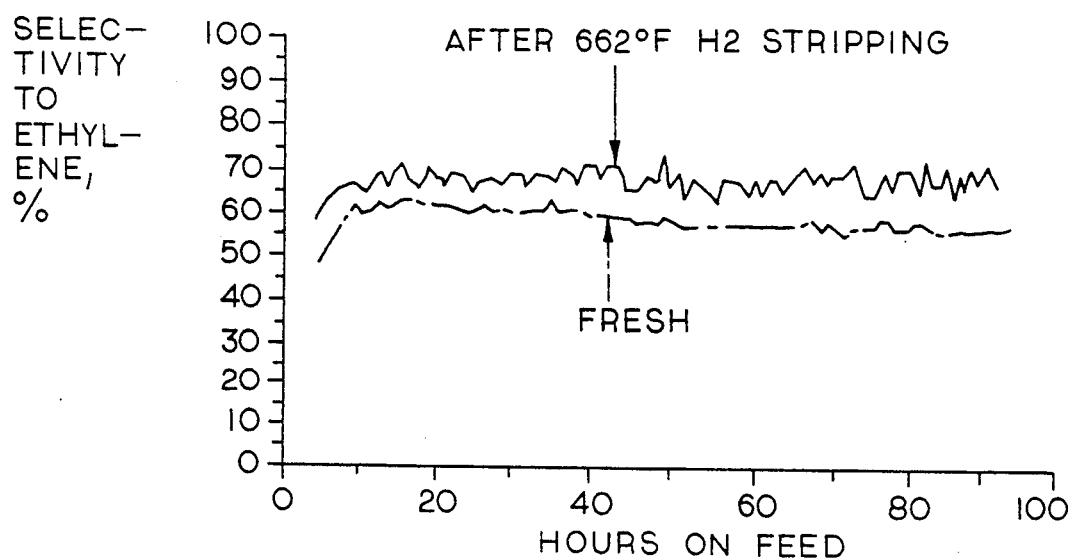
FIG. 3(c) is a graph comparing the selectivity to ethylene of the fresh and striped catalyst of Example 3.
Figure 3D:
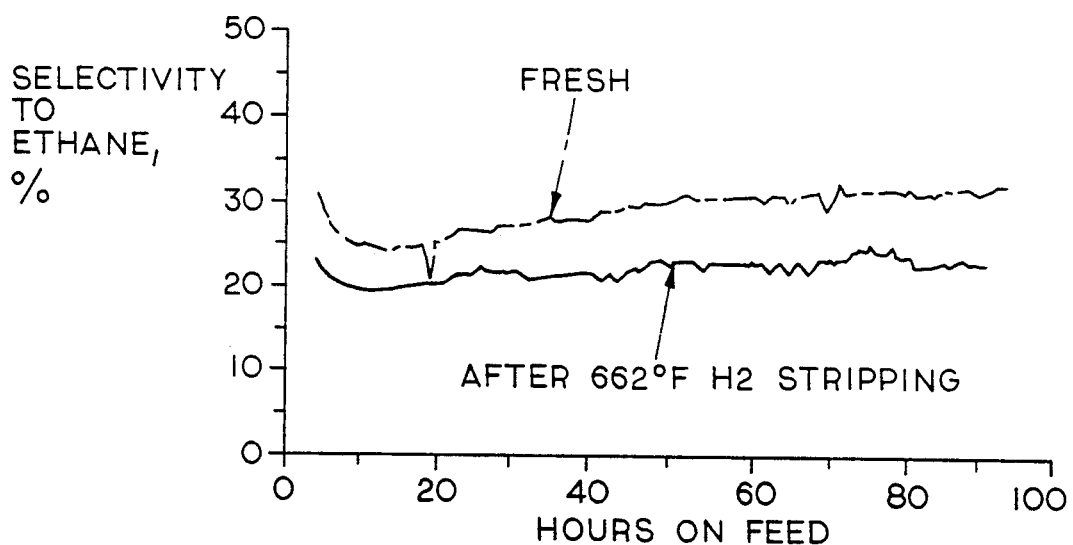
FIG. 3(d) is a graph comparing the selectivity to ethane of the fresh and stripped catalyst of Example 3.
Figure 3E:
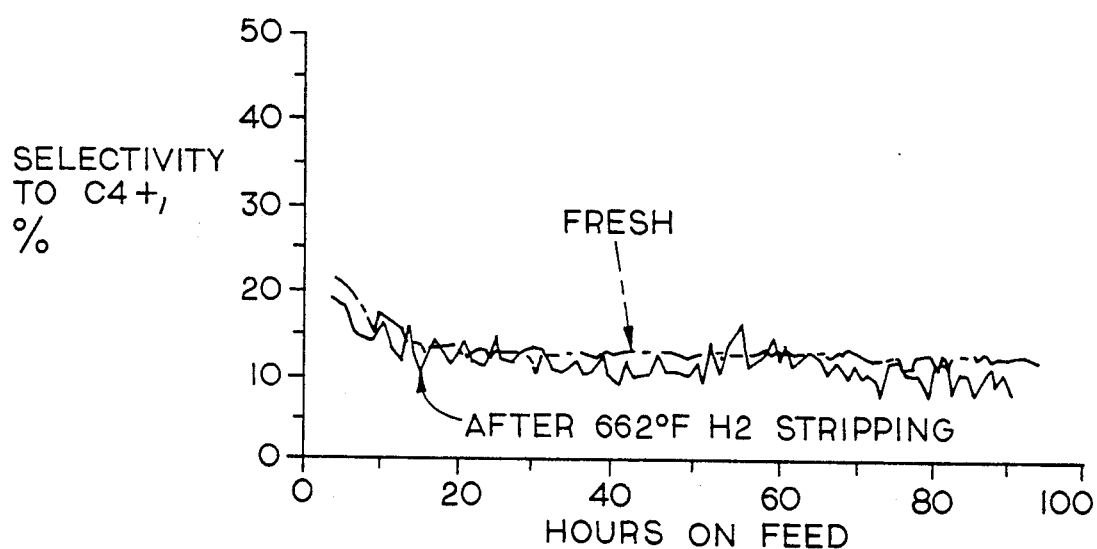
FIG. 3(e) is a graph comparing the selectivity to hydrocarbons having four or more carbon atoms of the fresh and stripped catalyst of Example 3.

A BASF HO11 catalyst ($Pd/SiO_2$) was subjected for 200 hours to the reaction conditions of 1.5% $C_2H_2$, 1.6 $H_2/C_2H_2$, 4000 GHSV, 2,068,428 Newtons/m$^3$ (300 psig), and about 66° C. (151° F.) average bed temperature. After 200 hours, the acetylene conversion of the catalyst decreased from 79% to 58%. The spent catalyst was then regenerated by hydrogen stripping for 16 hours with 5% $H_2/N_2$ at 2,068,428 Newtons/m$^3$ (300 psig) and about 350° C. (662° F.). After the hydrogen stripping, the acetylene conversion of the catalyst was 78%. A comparison of the catalyst activity before and after hydrogen stripping is plotted in FIG. 2. The results indicate that the hydrogen stripping at about 350° C. (662° F.) substantially fully regenerated the catalyst.

The temperature used during hydrogen stripping cannot be too high or else the palladium will begin to agglomerate. For example, when the catalyst was further hydrogen stripped at about 420° C. (788° F.) for 16 hours, the activity of the catalyst was reduced to 62% acetylene conversion—a dramatic decrease in catalyst activity.

EXAMPLE 3

A spent UCI G58E catalyst ($Pd/Ag/Al_2O_3$) was hydrogen stripped at about 350° C. (662° F.) and 1 atmospheric pressure with 9% $H_2/N_2$ for 24 hours. The performance of the hydrogen stripped catalyst was then compared to the performance of fresh catalyst at 70 hours into the activity test. The results are tabulated in Table I. The parameters of the activity test were 1.4% $C_2H_2$, 1.2 $H_2/C_2H_2$, 4900 GHSV, 2,068,428 Newtons/m$^3$ (300 psig), about 102° C. (215° F.) sandbath temperature.

TABLE I

|  | Fresh | $H_2$ Stripped |
|---|---|---|
| $C_2H_2$ Conversion | 80% | 80% |
| Selectivity to $C_2H_4$ | 57% | 67% |
| Selectivity to $C_2H_6$ | 32% | 23% |
| Selectivity to $C_4+$ | 11% | 10% |
| Deactivation Rate | −0.1%/hr | −0.2%/hr |

As seen from Table I, the hydrogen stripped catalyst unexpectedly had a selectivity to ethylene that was 10 points better than the activity of the fresh catalyst. Also, the ethane make was substantially reduced after hydrogen stripping. This result suggests that a "de-edging" process may have occurred which reduced the number of palladium sites responsible for overhydrogenating acetylene/ethylene to ethane.

Although the deactivation rate was higher for the hydrogen stripped catalyst, the deactivation rate can be overcome by more frequent hydrogen stripping. Even if more frequent hydrogen stripping is required to regenerate catalyst, the present process may be less time consuming and less damaging to the catalyst than frequent air burns.

One of skill in the art will appreciate that many modifications may be made to the embodiments described herein and explained in the accompanying figures without departing from the spirit of the present invention. Accordingly, the embodiments described herein are illustrative only and are not intended to limit the scope of the present invention.

We claim:

1. A method of substantially completely regenerating a catalyst comprising about 0.01 to 0.5% palladium that has been used to remove acetylenic impurities from an olefin stream and which has become at least partially deactivated for that use and whereby the selectivity of said catalyst to produce ethylene is enhanced consisting essentially of substantially stripping said catalyst of carbonaceous deposits using hydrogen at a linear velocity of at least about 15.2 cm/second (0.5 feet per second) and at a temperature in the range of about 600°–700° F. wherein said stripping occurs in the absence of an oxygenation step.

2. The method of claim 1 wherein said palladium comprises about 0.02 to about 0.05% of said catalyst.

3. The method of claim 1 wherein said catalyst has been used to remove acetylenic impurities from ethylene.

4. The method of claim 2 wherein said catalyst has been used to remove acetylenic impurities from ethylene.

5. The method of claim 4, wherein said temperature range is between about 660° F.

6. The method of claim 1, wherein said hydrogen comprises between about 5 to 10% of a combination of hydrogen and inert gas.

* * * * *

UNITED STATES PATENT AND TRADEMARK OFFICE
CERTIFICATE OF CORRECTION

PATENT NO. : 5,332,705
DATED : July 26, 1994
INVENTOR(S) : Yao-Jyh Huang, et. al.

It is certified that error appears in the above-indentified patent and that said Letters Patent is hereby corrected as shown below:

Title page, item [75], inventor: "Chong F. Shun" should be-- "Shun C. Fur

Signed and Sealed this

Eighteenth Day of April, 1995

Attest:

BRUCE LEHMAN

*Commissioner of Patents and Trademarks*

*Attesting Officer*

UNITED STATES PATENT AND TRADEMARK OFFICE
CERTIFICATE OF CORRECTION

PATENT NO. : 5,332,705
DATED : July 26, 1994
INVENTOR(S) : Yao-Jyh Robert Huang et al.

It is certified that error appears in the above-identified patent and that said Letters Patent is hereby corrected as shown below:

On the title page, item [75] should read:

Inventors, line 2 --Chong F. Shun-- should read "Shun Chong Fung".

Signed and Sealed this

Twenty-fifth Day of May, 1999

Attest:

Q. TODD DICKINSON

*Attesting Officer*        *Acting Commissioner of Patents and Trademarks*